United States Patent
Hill, Jr. et al.

(10) Patent No.: US 9,771,777 B2
(45) Date of Patent: *Sep. 26, 2017

(54) TUBING RETRIEVABLE INJECTION VALVE ASSEMBLY

(71) Applicant: Tejas Research and Engineering, LLC, The Woodlands, TX (US)

(72) Inventors: Thomas G. Hill, Jr., Conroe, TX (US); Robert C. Henschel, The Woodlands, TX (US)

(73) Assignee: Tejas Research & Engineering, LLC, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/099,286

(22) Filed: Apr. 14, 2016

(65) Prior Publication Data

US 2016/0230506 A1    Aug. 11, 2016

Related U.S. Application Data

(63) Continuation of application No. 13/669,059, filed on Nov. 5, 2012, now Pat. No. 9,334,709.

(60) Provisional application No. 61/639,569, filed on Apr. 27, 2012.

(51) Int. Cl.
| | | |
|---|---|---|
| *E21B 34/10* | (2006.01) | |
| *E21B 43/16* | (2006.01) | |
| *E21B 43/20* | (2006.01) | |
| *G06F 19/00* | (2011.01) | |
| *E21B 34/00* | (2006.01) | |

(52) U.S. Cl.
CPC ............ *E21B 34/10* (2013.01); *E21B 34/102* (2013.01); *E21B 43/16* (2013.01); *E21B 43/20* (2013.01); *G06F 19/3406* (2013.01); *E21B 2034/005* (2013.01)

(58) Field of Classification Search
CPC .... E21B 34/102; E21B 34/105; E21B 34/106; E21B 34/107; E21B 34/10; E21B 43/20; E21B 43/16; E21B 2034/005; G06F 19/3406

See application file for complete search history.

(56) References Cited

U.S. PATENT DOCUMENTS

| | | |
|---|---|---|
| 3,724,475 A | 4/1973 | Ruppel |
| 3,973,587 A | 8/1976 | Cochran |
| 4,069,871 A | 1/1978 | Page, Jr. |

(Continued)

OTHER PUBLICATIONS

USPTO Notice of Allowance for U.S. Appl. No. 14/697,289 dated Aug. 11, 2016.

(Continued)

*Primary Examiner* — Michael Wills, III
(74) *Attorney, Agent, or Firm* — Tumey L.L.P.

(57) ABSTRACT

A method and apparatus for controlling the flow of fluid in an injection well includes a main valve assembly having a valve and a retrievable nozzle selective lock assembly (RNSLA). The RNSLA is operable when positioned within the valve body to open the valve when fluid is pumped into the well and closes the valve when fluid flow is terminated. The RNSLA includes a replaceable orifice nozzle so that orifices of different dimensions may be used in conjunction with the valve assembly. In an alternate embodiment, the RNSLA includes a variable output nozzle assembly to maintain the valve in a protected open position without chattering over a wide range of flow rates.

9 Claims, 7 Drawing Sheets

(56) References Cited

U.S. PATENT DOCUMENTS

| | | |
|---|---|---|
| 4,137,933 A | 2/1979 | Culpepper |
| 4,362,214 A | 12/1982 | Pringle et al. |
| 4,416,301 A | 11/1983 | Brumm |
| 4,585,067 A | 4/1986 | Blizzard et al. |
| 4,601,342 A | 7/1986 | Pringle |
| 4,624,315 A | 11/1986 | Dickson et al. |
| 5,004,007 A | 4/1991 | Johnson et al. |
| 5,095,994 A | 3/1992 | Dollison |
| 5,190,106 A | 3/1993 | Johnston |
| 6,415,509 B1 | 7/2002 | Echols et al. |
| 6,514,408 B1 | 2/2003 | Simone |
| 6,799,686 B2 | 10/2004 | Echols et al. |
| 6,971,405 B2 | 12/2005 | Pickelman |
| 7,287,684 B2 | 10/2007 | Blackburne, Jr. |
| 7,578,344 B2 | 8/2009 | Hopkins et al. |
| 7,614,452 B2 | 11/2009 | Kenison et al. |
| 7,703,532 B2 | 4/2010 | O'Malley et al. |
| 7,814,982 B2 | 10/2010 | Moyes |
| 7,866,401 B2 | 1/2011 | McCalvin |
| 8,365,753 B2 | 2/2013 | Dana |
| 2006/0162932 A1 | 7/2006 | McCalvin |
| 2006/0278395 A1 | 12/2006 | Kenison et al. |
| 2007/0256834 A1 | 11/2007 | Hopkins et al. |
| 2008/0236842 A1 | 10/2008 | Bhavsar et al. |
| 2009/0065215 A1 | 3/2009 | Tveiten et al. |
| 2012/0312540 A1 | 12/2012 | Lefebvre |

OTHER PUBLICATIONS

Australian Patent Examination Report No. 1 for Australian Patent Application No. 2013251422 dated Aug. 25, 2016.
Notice of Allowance for U.S. Appl. No. 14/941,623 dated Dec. 20, 2016.
Final Office Action for U.S. Appl. No. 13/863,063 dated Jun. 11, 2015.
Office Action for U.S. Appl. No. 13/863,063 dated Apr. 8, 2015.
International Search Report and Written Opinion for International Application No. PCT/US2013/038438 dated Aug. 16, 2013.
Schlumberger publication "TRTO Series Injection Safety Valves" 2009.
Schlumberger publication "A-Series Injection Valves" 2009.
Office Action for U.S. Appl. No. 13/669,059 dated Apr. 16, 2015.
Final Office Action for U.S. Appl. No. 13/669,059 dated Oct. 14, 2015.
Notice of allowance for U.S. Appl. No. 13/669,059 dated Jan. 8, 2016.
EPO Search Report for Application No. 13781010.7 dated Nov. 17, 2015.
Notice of Allowance for U.S. Appl. No. 13/863,063 dated Aug. 14, 2015.
Office Action for U.S. Appl. No. 14/697,289 dated Jan. 11, 2016.
USPTO Final Office Action for U.S. Appl. No. 14/941,623 dated Nov. 7, 2016.
Non-final Rejection for U.S. Appl. No. 15/353,495 dated Jun. 14, 2017.

TUBING RETRIEVABLE INJECTION VALVE ASSEMBLY

This application is a continuation application of Ser. No. 13/669,059 filed Nov. 5, 2012 which claims priority to provisional application Ser. No. 61/639,569 with a filing date of Apr. 27, 2012.

BACKGROUND OF INVENTION

Field of the Invention

This invention is directed to an injection valve typically used in conjunction with an injection well. Injection wells are drilled for example in close proximity to producing oil or gas wells that have peaked in terms of their output. Fluid for example water is pumped under pressure into the injection well which in turn acts to force the oil or gas into the producing wells thus increasing the yield.

Description of Related Art

U.S. Pat. No. 7,866,401 discloses an injection safety valve having a restrictor to create a pressure differential so as to move a flow tube past a flapper valve. The diameter of the restrictor is if fixed.

BRIEF SUMMARY OF THE INVENTION

The invention includes providing a tubing retrievable injection valve having a full bore internal diameter when running and retrieving the valve. A slick line retrievable nozzle having an orifice is carried by a retrievable nozzle selective lock assembly. The nozzle assembly is retrievable without removing the injection valve. Consequently the diameter of the nozzle may be changed on the surface. The injection valve also has a temporary lock out feature so that the valve may be placed in the well in a lock out mode. In certain situations where the flow rate of the water may vary, an embodiment of the invention includes a nozzle assembly with a variable orifice to provide an infinitely variable downhole nozzle that will minimize the pressure drop during injection over a range of injection flow rates. The nozzle is designed to generate a pressure drop sufficient to hold the flapper valve fully open. This prevents the flapper valve from "chattering" and isolates the flapper valve from fluid flow during injection both of which are harmful to the flapper valve assembly.

The variable output nozzles are designed so that as flow occurs, the flow tube will first move in a direction to open the flapper valve and then the output area of the nozzle will increase with increased flow rates.

The nozzle assembly can either be run pre-installed in the injection valve prior to running or after the injection valve has been set, utilizing wireline/slickline operations to insert and or remove the nozzle assembly from the injection valve.

DETAILED DESCRIPTION OF THE INVENTION

Figure 1:
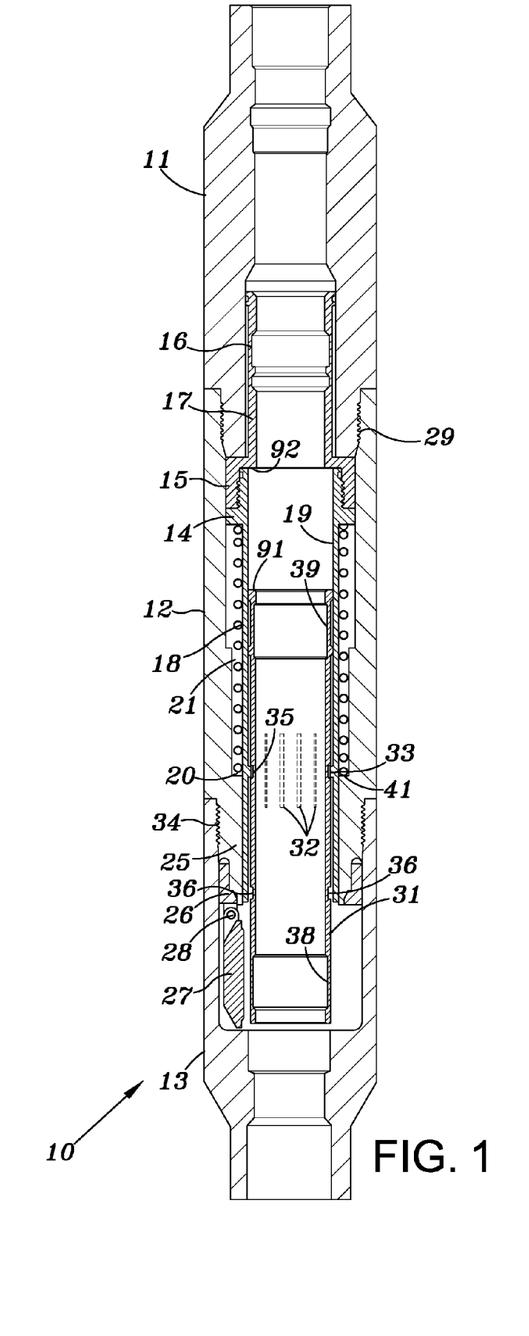
FIG. 1 is a cross sectional view of an embodiment of the valve in a lock out, running position.

Referring to FIG. 1, an embodiment of the injection valve 10 includes a pressure containing body comprising an upper valve body member 11, a tubular middle valve body member 12 suitably attached to the upper valve body member 11 by threads at 29, for example, and a lower valve body member 13 which is connectable to a tubular at its downhole end. Valve body members 12 and 13 are secured to each other by threads for example at 34.

The injection valve 10 further includes an upper flow tube having a first section 17 and a second section 19 which are secured together. Section 17 has an interior nipple profile at 16 for receiving a tool. Second section 19 extends to valve seat 26 when the valve is in the position shown in FIG. 1. Second section 19 includes a plurality of slots 32 as shown in FIG. 1. Ridges 33 are formed on the inner surface of second section 19 around slots 32 thus forming a collet. A shiftable lower flow tube 31 is positioned within the elongated sleeve portion 19 of the upper flow tube. Shiftable lower flow tube 31 has two annular grooves 35 and 36 on its outer periphery located so as to form a profile for engagement with ridges 33 on the inner surface of second section 19. Shiftable flow tube 31 also has shifting profiles 39 and 38 at each end thereof.

Middle body member 12 has a reduced diameter portion 25 that carries an annular valve seat 26. A flapper valve 27 is pivotably connected at 28 to valve seat 26 and is resiliently biased to a closed position on valve seat 26 as is known in the art.

A coil spring 18 is positioned about second section 19 and is captured between shoulder 14 of the upper flow tube and an internal shoulder 41 provided within middle valve body member 12.

In the temporary lock out running position shown in FIG. 1, shiftable flow tube 31 is positioned within the valve body so as to extend beyond valve seat 26 thereby maintaining flapper valve 27 in an open position.

Figure 2:
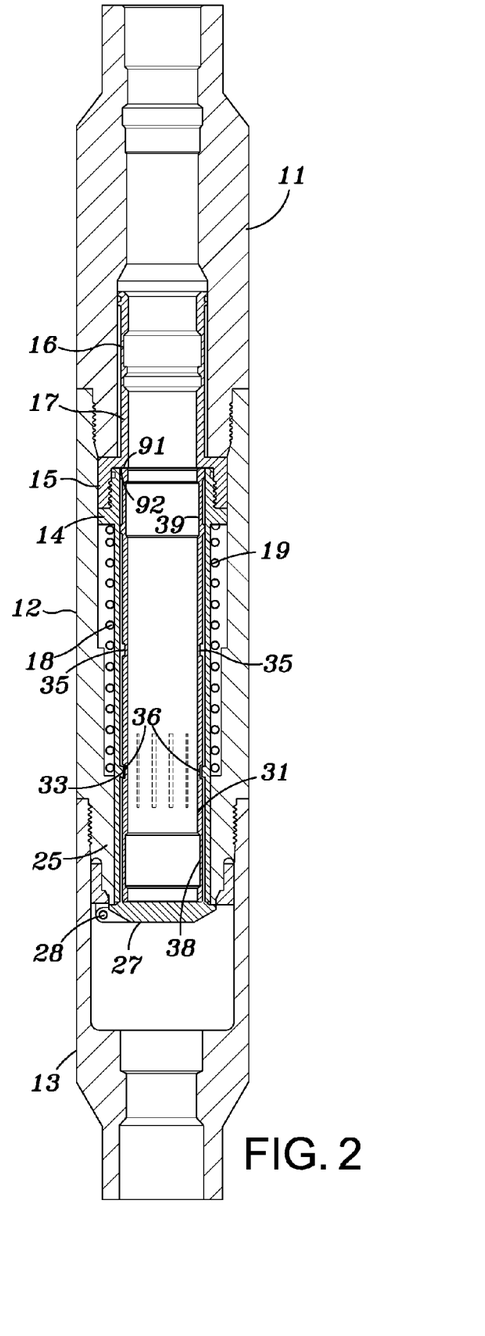
FIG. 2 is a cross sectional view of an embodiment of the valve in a pre-injection position with the valve member closed.

When the valve is positioned within the well at the desired location, a suitable running tool is lowered into the well and engages the upper shifting profile 39 of shiftable flow tube 31 and the flow tube is moved upwardly, to the position shown in FIG. 2. The uphole end portion 91 of the shiftable lower flow tube 31 will abut a shoulder portion 92 of the upper flow tube 15 as shown in FIG. 2. In this position, the resiliently biased flapper valve will be in the closed position.

The retrievable nozzle selective lock assembly (RNSLA) will now be discussed with reference to FIGS. 3 and 4. The RNSLA 50 includes a sleeve formed by generally cylindrical members 51, 52, and 53 having an interior flow passage 61. An inner tubular member 56 is located within cylindrical member 52 and carries nozzle 53. A plurality of selective locking dogs 58 are located around a portion of its periphery as shown in FIG. 4. Leaf springs 59 are positioned under locking dogs 58. RNSLA 50 includes an annular packing assembly 55. A replaceable and retrievable orifice nozzle 53 is releaseably attached to the body portion of the RNSLA and includes an orifice 54. Nozzle 53 may be replaced on the surface with another nozzle having a different size orifice 54.

Figures 5, 6:
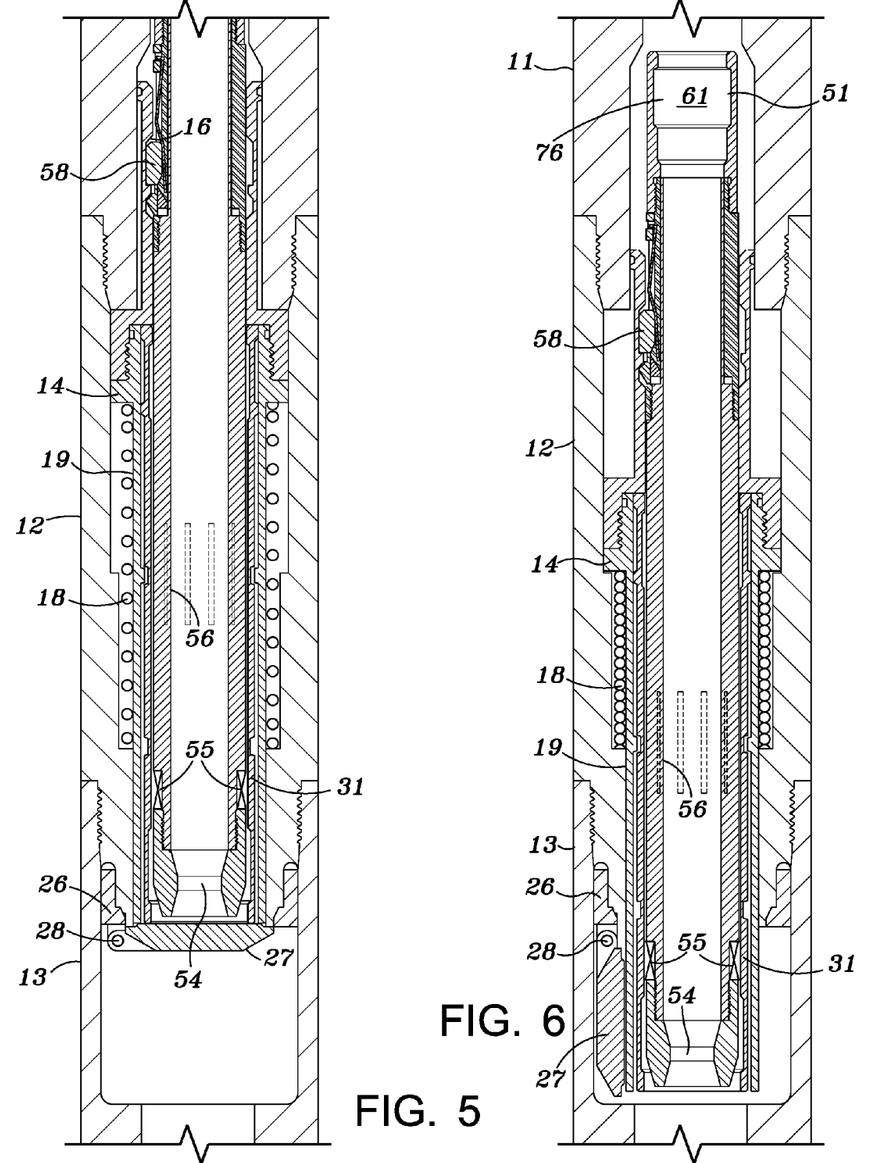
FIG. 5 is a cross sectional view of a valve showing the retrievable nozzle selective lock assembly located within the valve body.
FIG. 6 is a cross sectional view of a valve in an open injection position.

FIG. 5 illustrates the position of the RNSLA within the injection valve prior to the injection stage. RNSLA may be lowered into the valve body by a suitable tool to a position where the selective locking dogs 58 engage the selective nipple profile 16 in first section 17. At this point the RNSLA will be physically connected to the upper flow tube; however flapper valve 27 is still in the closed position.

The next step in the process is to pump a fluid such as water under pressure into the valve body. As the fluid flows through the RNSLA, a pressure drop will occur across orifice 54 which will cause the RNSLA and the upper flow tube as well as shiftable flow tube 31 to move downhole as shown in FIG. 6.

This movement will compress spring 18. The downhole portions of both the upper flow tube and lower flow tube will be forced into contact with flapper valve 27 and as they are moved further by the pressure differential, they will open the flapper valve to the position as shown in FIG. 6.

As long as the fluid is being pumped the injection valve will remain open. However when the pumping stops, compressed spring 18 will move the RNSLA and the upper and lower flow tubes back to the position shown in FIG. 5 in which the flapper valve is in the closed position.

Figure 7:
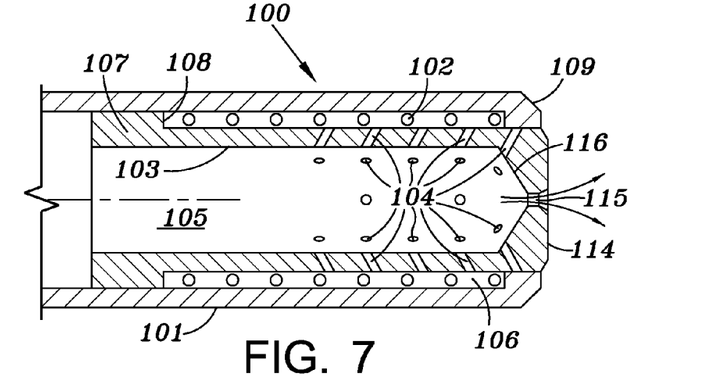
FIG. 7 is a cross-sectional view of a second embodiment of a retrievable nozzle selection lock assembly according to the invention.

FIG. 7 illustrates a second embodiment of the invention. In this case a variable output nozzle assembly 100 replaces the nozzle 53 shown in FIGS. 3 and 4.

Variable output nozzle assembly 100 includes an outer tubular cylindrical casing 101. An axially moveable cylindrical sleeve 103 having an enlarged portion 107 is positioned within casing 101 and has an end face 114 that extends outwardly of casing 101. Sleeve 103 has an interior flow passage 105 and also has a plurality of outlet ports 104 that are axially and radially spaced about its longitudinal axis. Sleeve 103 terminates in an end face 116 that includes an outlet orifice 115. A coil spring 102 is positioned between the inner surface of casing 101 and the outer surface of sleeve 103 as shown in FIG. 7. In the relaxed position of FIG. 7, one end of the coil spring 102 abuts against shoulder 108 on enlarged portion 107 of sleeve 103 and the other end abuts against end face 109 of the casing 101.

Figure 8:
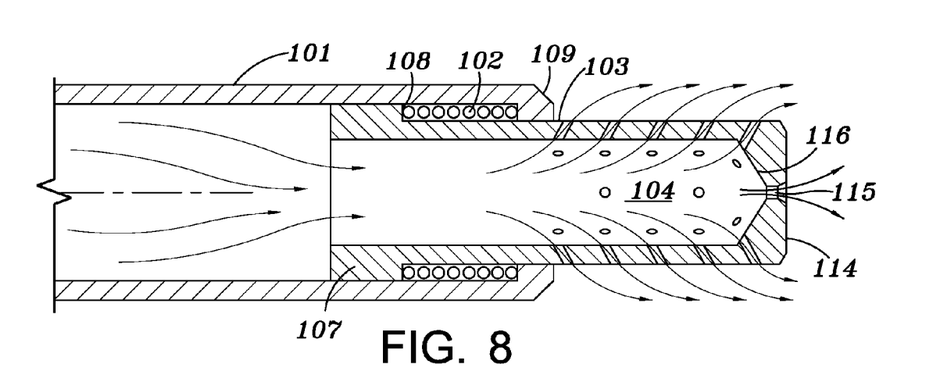
FIG. 8 is a cross-sectional view of the embodiment of FIG. 7 shown in a fully open condition.

At lower flow rates, the pressure drops across orifice 115 will be sufficient to move the lower flow tube to a position keeping flapper valve 27 open. As the flow rate increases, sleeve 103 is moved axially to sequentially move outlet ports 104 past the end face 109 of casing 101 as shown in FIG. 8, thereby allowing more fluid to exit the nozzle to proceed downhole of the flapper valve.

Figure 9:
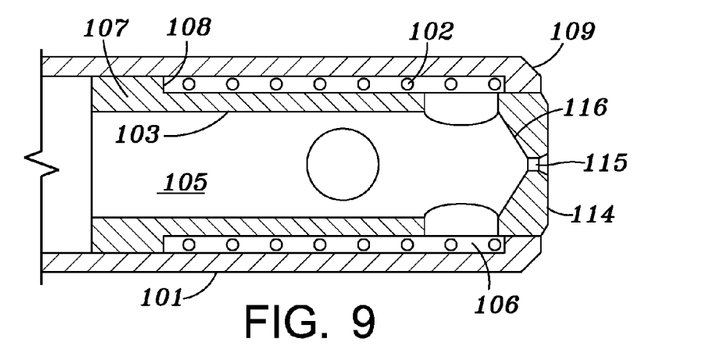
FIG. 9 is a cross-sectional view of a third embodiment of a retrievable nozzle selective lock assembly according to the invention.

FIG. 9 illustrates a variation from the shape and location of the outlet ports. In this embodiment outlet ports may be of the outlet ports. In this embodiment outlet ports may be relatively large circular openings 114 that are axially offset with respect to one another. Openings 114 may also be elliptical or wedged shape or of any geometric shape.

The spring constants of springs 18 and 102 are chosen so that as fluid flow begins, the RNSLA will first move in a downhole direction opening the flapper valve before sleeve 103 moves in a downhole direction.

Figure 10:
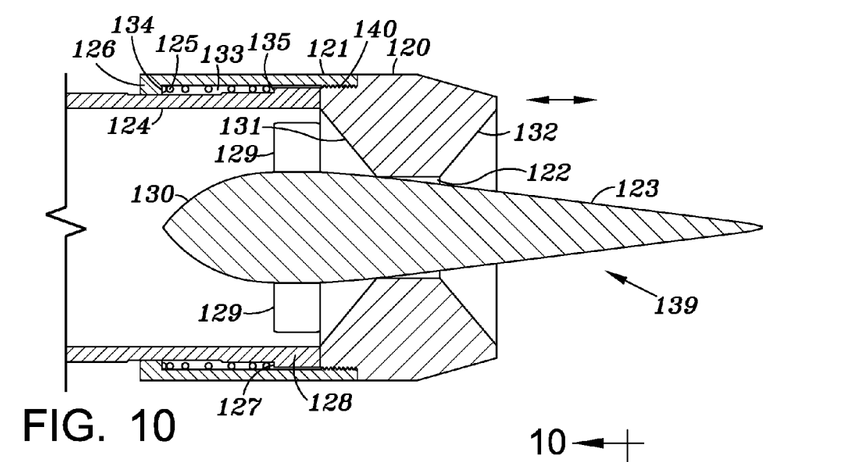
FIG. 10 is a cross-section view along line 10-10 of FIG. 11 of a fourth embodiment of a retrievable nozzle selective lock assembly according to the invention.
Figures 11, 12:
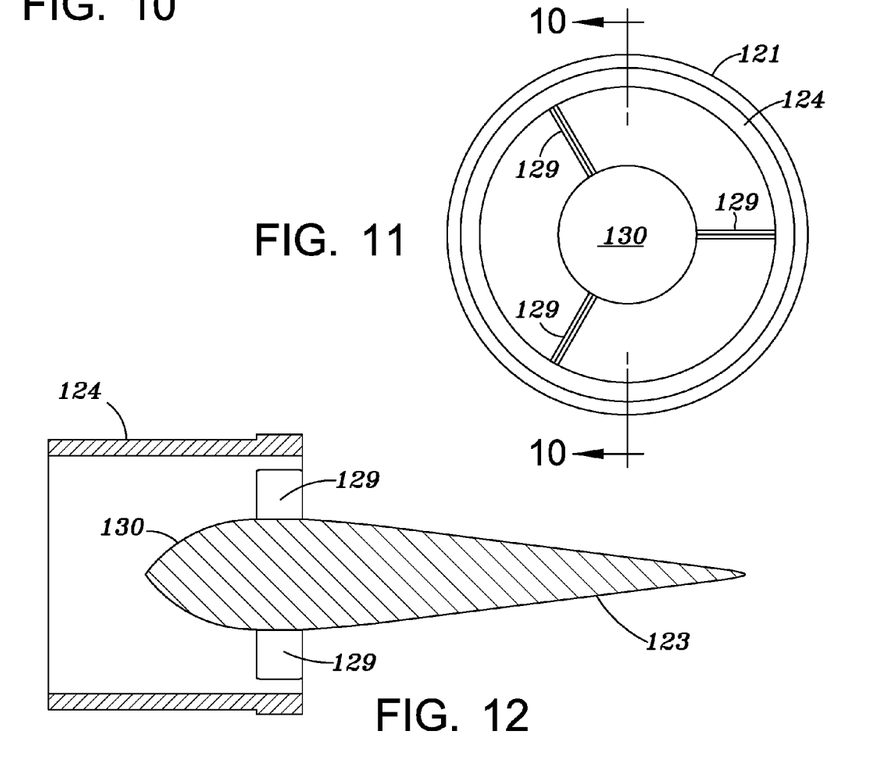
FIG. 11 is an end view of the retrievable nozzle assembly of FIG. 10.
FIG. 12 is a cross-sectional view of the nozzle core member of the embodiment of FIG. 10.

FIGS. 10-12 illustrate yet a further embodiment of the invention.

In this embodiment the variable output nozzle assembly includes a first fixed portion including a cylindrical tubular casing 124 having a solid conical core member 139 supported therein by a plurality of struts 129 as shown in FIGS. 11 and 12. An outer tubular sleeve member 120 is fitted over casing 124 and includes a constricted portion 122 and conical portions 131 and 132 on either side of constricted portion 122. Conical member 139 has a first enlarged portion 130 followed by a tapered cone portion 123. Outer sleeve member 120 includes a thin walled portion 121 that extends to an annular shoulder 126 such that an annular space 133 is formed between casing 124 and thin walled portion 121. A coil spring 125 is positioned within space 133 such that one end of the spring abuts against a shoulder 134 on enlarged portion 126 of thin walled portion 121 and abuts against a shoulder 135 provided on tubular casing 124. Thin wall portion 121 is detachably secured to outer sleeve member 12 at 140 for example by threads. In the position shown in FIG. 10, the outer surface of core member 139 engages constriction 122 so as to prevent flow.

As the flow rate of fluid is increased, outer sleeve member 120 will move to the right as viewed in FIG. 10. Due to the tapering of cone section 123, the outlet area of the nozzle at 122 will increase as the flow rate increases. Thus at lower flow rates sufficient force will be provided to maintain the flapper valve in the open position as well as at high flow rates.

The embodiments according to FIGS. 7-12 provide an infinitely variable nozzle which will minimize pressure drop over a range of injection flow rates. They provide full open flapper protection over the full range of injection rates thus eliminating flapper chatter due to partial valve opening during injection.

Figure 3:
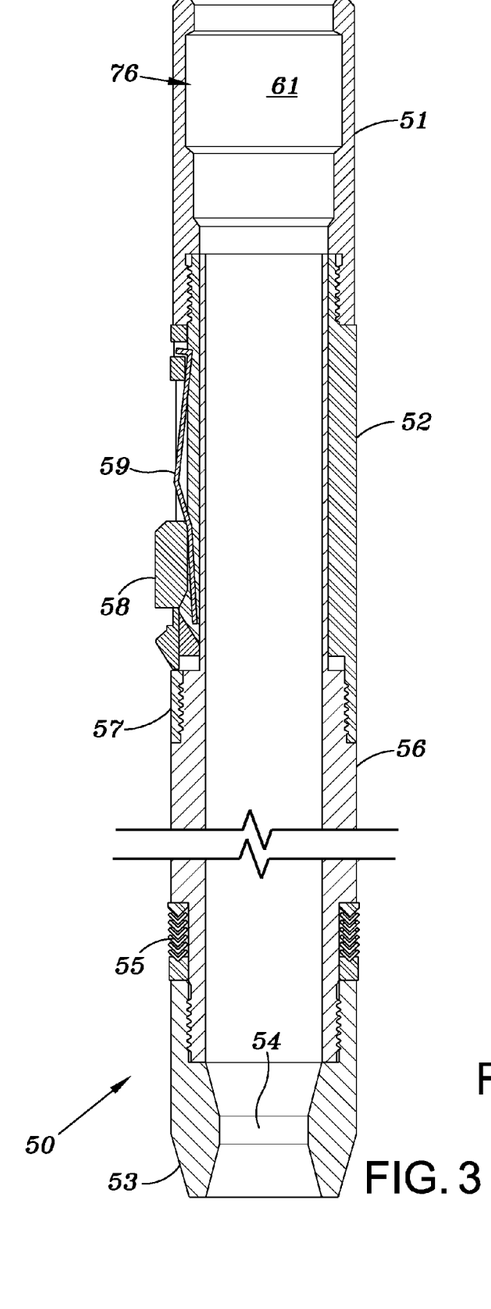
FIG. 3 is a cross-sectional view of the retrievable orifice selective lock assembly.
Figure 4:
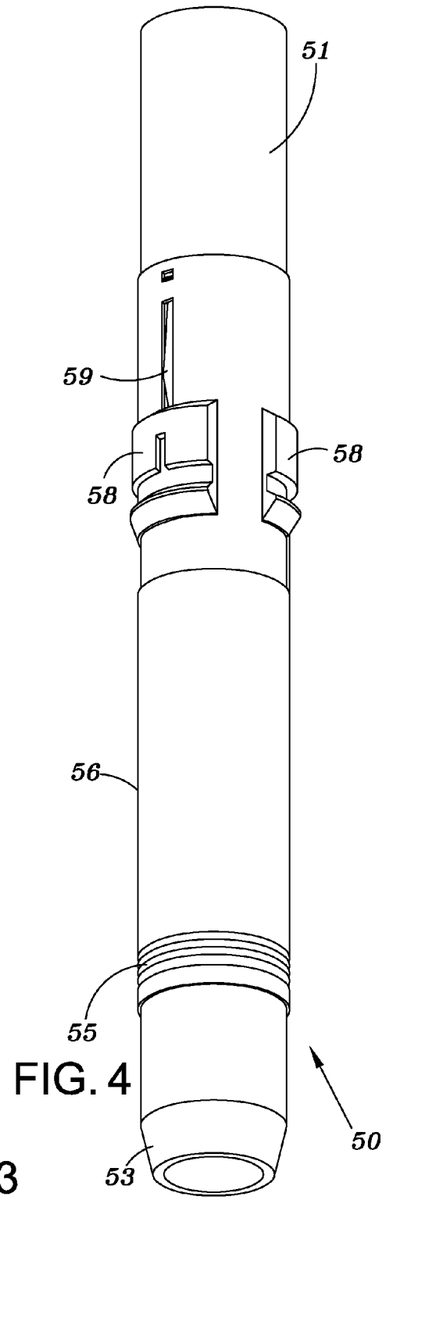
FIG. 4 is a perspective view of the retrievable nozzle selective lock assembly.

The variable output nozzles of FIGS. 7-12 can be substituted for the nozzle 53 shown in FIG. 3 so that they can be placed and retrieved as a part of the RNSLA shown in FIGS. 3 and 4.

Figures 13, 14:
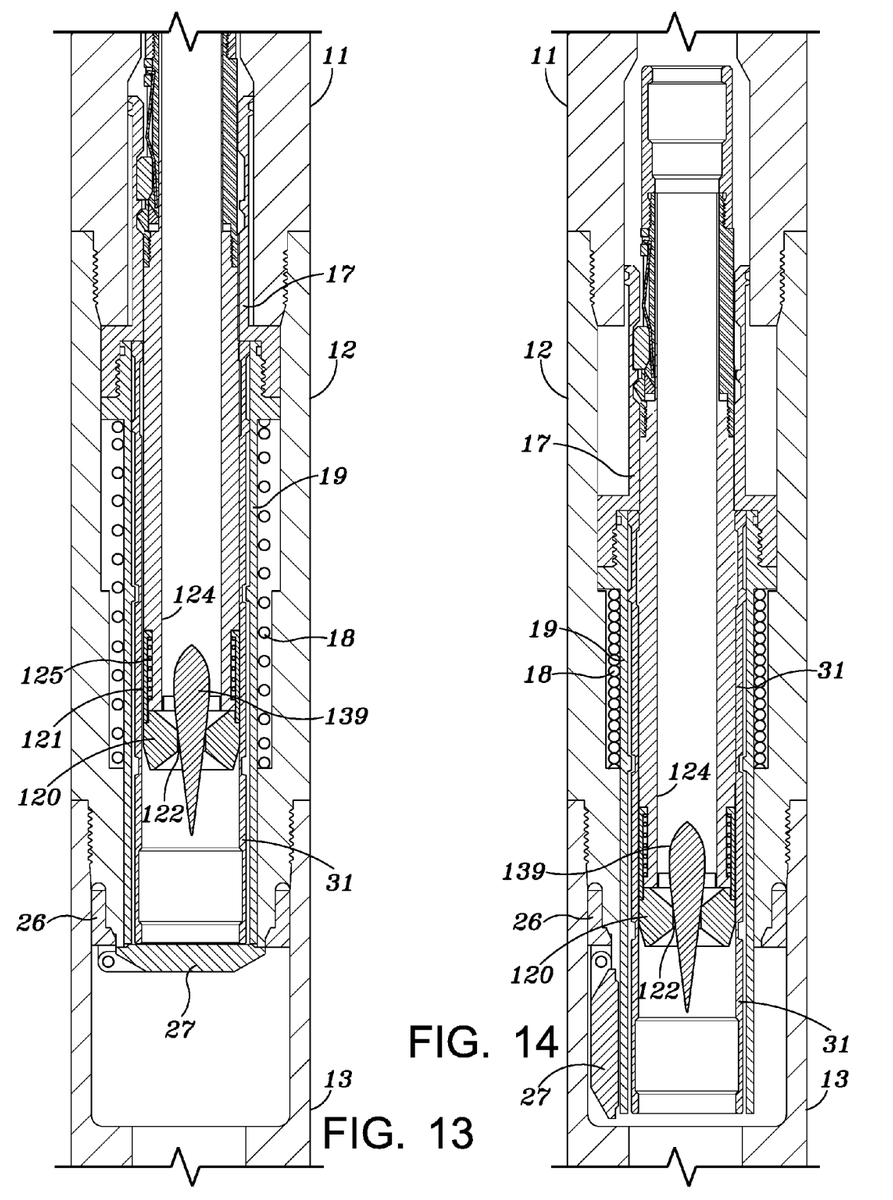
FIG. 13 is a cross-sectional view of an embodiment of the valve according to the invention with the variable nozzle assembly of the embodiment shown in FIG. 10 I the closed position.
FIG. 14 is a cross-sectional view of the embodiment shown in FIG. 13 with the flapper valve in the open position.
Figure 15:
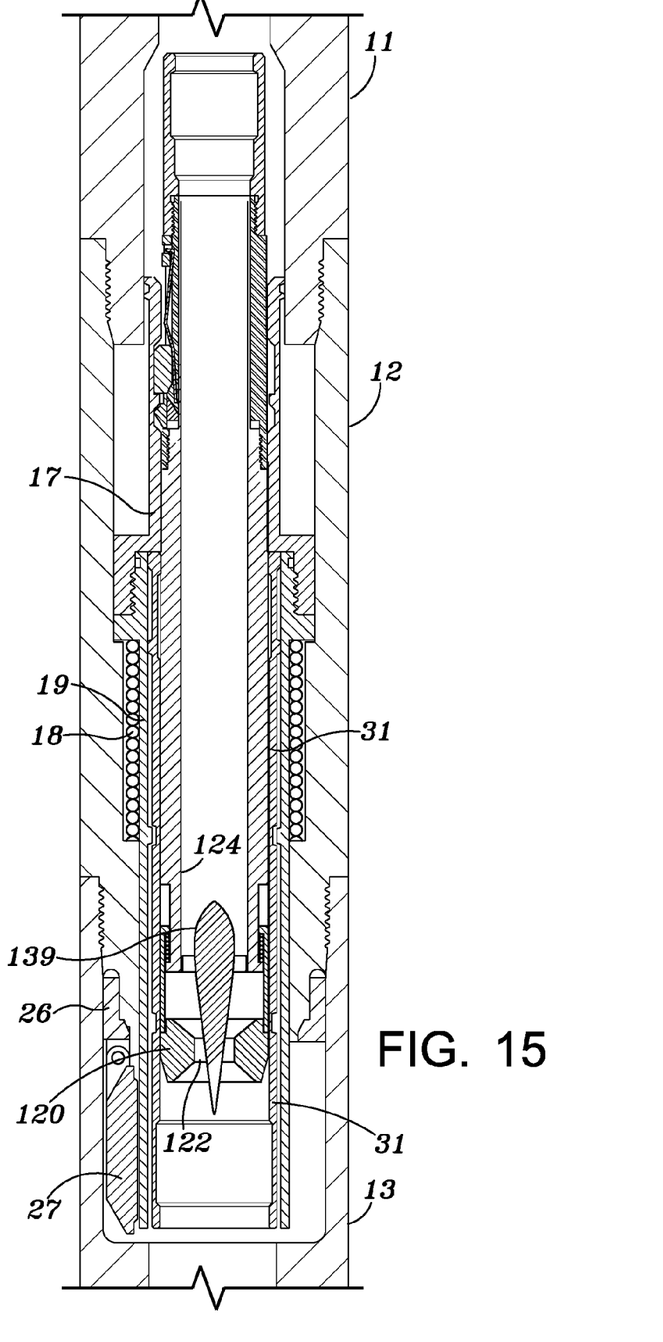
FIG. 15 is a cross-sectional view of the embodiment shown in FIG. 13 with the flapper valve in the open position and the variable orifice in the open position.

FIGS. 13-15 shown the sequential opening of the flapper valve and the variable orifice as flow is initiated in the well according to the embodiment of the variable orifice shown in FIG. 10. The difference between FIGS. 5 and 6 and FIGS. 13-15 is that the nozzle assembly 53 of FIGS. 5 and 6 has been replaced by the nozzle assembly of FIG. 10.

In the position shown in FIG. 13, the flapper valve 27 is closed and the outer surface of core member 139 engages constriction 122 so as to prevent flow through the nozzle. The lower ends of upper flow tube 10 and lower flow tube 31 are positioned adjacent the flapper valve 27. As fluid flow begins the upper and lower flow tubes along with the variable orifice nozzle assembly will move downwardly due to fluid pressure thereby comprising spring 18. The spring constants for spring 18 an spring 125 are selected so that during initial fluid flow the upper and lower flow tube as well as the variable orifice nozzle assembly will move to the position shown in FIG. 4 with the variable orifice 122 still in a closed position. However, as fluid pressure and flow increases, outer sleeve member 120 will move downwardly with respect to tubular casing 124 in which cone member 139 is fixed to the position shown in FIG. 15. In this position fluid will flow through variable orifice 122.

All of the embodiments may be deployed or retrieved using a wireline or slickline and are easily redressable and repairable. Furthermore, when injection flow is stopped the valve automatically will close, thereby protecting the upper completion from back flow or a blowout condition.

Although the present invention has been described with respect to specific details, it is not intended that such details should be regarded as limitations on the scope of the invention, except to the extent that they are included in the accompanying claims.

We claim:

1. A valve assembly for controlling the flow of fluid within an injection well comprising:
    a valve body,
    an upper flow tube within the body;
    a lower flow tube positioned within the valve body;
    a valve located in the valve body, and
    a retrievable nozzle selective lock assembly positionable within the valve body and operable to open the valve when fluid flow is initiated through the valve body and operable to close the valve when fluid flow is terminated, wherein the retrievable nozzle selective lock assembly includes a variable orifice, wherein the variable orifice comprises an outer tubular casing and an axially movable sleeve positioned within the outer casing, said axially movable sleeve having an internal flow passage and a plurality axially spaced outlet ports.

2. The valve assembly of claim 1 wherein said retrievable nozzle selective lock assembly may be retrieved from the injection well while leaving said valve in the well in a closed position.

3. The valve assembly of claim 2 wherein said lower flow tube is adapted to be shifted to a first position to lock the valve in the open position.

4. The valve assembly of claim 2 wherein, said upper flow tube is adapted to return the valve to a closed position.

5. The valve assembly of claim 1 wherein the lower flow tube is axially shiftable with respect to the valve body.

6. The valve assembly of claim 1 wherein the upper flow tube and the lower flow tube are axially movable within the valve assembly, and a spring overlying a portion of the upper flow tube and engaging a shoulder provided on the upper flow tube, whereby axial movement of the upper flow tube compresses the spring.

7. A valve assembly for controlling the flow of fluid within an injection well comprising:
    a valve body,
    an upper flow tube within the body;
    a lower flow tube positioned within the valve body;
    a valve located in the valve body, and
    a retrievable nozzle selective lock assembly positionable within the valve body and operable to open the valve when fluid flow is initiated through the valve body and operable to close the valve when fluid flow is terminated, wherein the retrievable nozzle selective lock assembly includes a variable orifice,
    the variable orifice includes a tubular casing have a core member supported within the tubular casing, an outer sleeve member axially movable on the tubular casing and including a constricted portion, the core member and constricted portion forming a variable orifice, and a spring positioned between the tubular casing and the outer sleeve member, whereby axial movement of the outer sleeve member compresses the spring.

8. The valve assembly of claim 7 wherein the variable orifice is initially biased to a closed position by the spring.

9. A valve assembly for controlling the flow of fluid within an injection well comprising:
    a valve body,
    an upper flow tube within the body;
    a lower flow tube positioned within the valve body;
    a valve located in the valve body, and
    a retrievable nozzle selective lock assembly positionable within the valve body and operable to open the valve when fluid flow is initiated through the valve body and operable to close the valve when fluid flow is terminated, wherein the retrievable nozzle selective lock assembly includes a variable orifice,
    a first spring in engagement with the upper flow tube to resist downward movement of the upper flow tube, and a second spring biased to initially close the variable orifice, wherein the spring constants of the first and second springs are chosen so that the valve at the downhole end of the valve body will open first and as a flow rate of fluid is increased, the variable orifice will open to permit fluid flow through the value assembly.

* * * * *